US009562908B2

(12) United States Patent
Yoshida et al.

(10) Patent No.: US 9,562,908 B2
(45) Date of Patent: Feb. 7, 2017

(54) ORGANIC COLORED MICROPARTICLES, DIAGNOSTIC REAGENT KIT CONTAINING THE SAME, AND IN VITRO DIAGNOSIS METHOD

(71) Applicant: ASAHI KASEI FIBERS CORPORATION, Osaka-shi, Osaka (JP)

(72) Inventors: Satoru Yoshida, Tokyo (JP); Yoshiyuki Shiomi, Tokyo (JP); Toshihiko Matsui, Tokyo (JP); Masanori Doi, Tokyo (JP); Nobuyuki Mimura, Tokyo (JP); Takeshi Matsuse, Tokyo (JP)

(73) Assignee: ASAHI KASEI FIBERS CORPORATION, Osaka-Shi (JP)

( * ) Notice: Subject to any disclaimer, the term of this patent is extended or adjusted under 35 U.S.C. 154(b) by 0 days.

(21) Appl. No.: 14/460,331

(22) Filed: Aug. 14, 2014

(65) Prior Publication Data
US 2015/0111307 A1 Apr. 23, 2015

Related U.S. Application Data

(63) Continuation of application No. 13/510,253, filed as application No. PCT/JP2010/070369 on Nov. 16, 2010, now abandoned.

(30) Foreign Application Priority Data

Nov. 17, 2009 (JP) ................................. 2009-262004
Jul. 16, 2010 (JP) ................................. 2010-161866

(51) Int. Cl.
  *G01N 33/548* (2006.01)
  *G01N 33/58* (2006.01)
  *G01N 33/558* (2006.01)

(52) U.S. Cl.
  CPC .......... *G01N 33/587* (2013.01); *G01N 33/548* (2013.01); *G01N 33/558* (2013.01); *G01N 33/585* (2013.01); *G01N 2333/59* (2013.01); *G01N 2458/00* (2013.01); *Y10T 428/2982* (2015.01)

(58) Field of Classification Search
  None
  See application file for complete search history.

(56) References Cited

U.S. PATENT DOCUMENTS

| | | | |
|---|---|---|---|
| 4,166,105 A | 8/1979 | Hirschfeld | |
| 4,373,932 A | 2/1983 | Gribnau et al. | |
| 5,120,643 A | 6/1992 | Ching et al. | |
| 5,266,497 A | 11/1993 | Imai et al. | |
| 5,298,430 A * | 3/1994 | Myers et al. | 436/530 |
| 6,156,271 A | 12/2000 | May | |
| 6,327,410 B1 | 12/2001 | Walt et al. | |
| 7,179,660 B1 | 2/2007 | Kirakossian et al. | |
| 9,096,690 B2 * | 8/2015 | Shiomi | C08B 1/006 |
| 2002/0127603 A1 | 9/2002 | Basiji et al. | |
| 2002/0142485 A1 | 10/2002 | Liu et al. | |
| 2005/0032244 A1 * | 2/2005 | Nie et al. | 436/518 |
| 2005/0100968 A1 | 5/2005 | Gallop et al. | |
| 2005/0130240 A1 * | 6/2005 | Lin et al. | 435/7.32 |
| 2006/0286683 A1 | 12/2006 | Hermann et al. | |
| 2007/0141727 A1 | 6/2007 | Huang et al. | |
| 2010/0087552 A1 | 4/2010 | Shiomi et al. | |
| 2011/0020954 A1 | 1/2011 | Shiomi et al. | |
| 2011/0136099 A1 | 6/2011 | Schneider et al. | |

FOREIGN PATENT DOCUMENTS

| | | |
|---|---|---|
| EP | 2 103 644 A1 | 9/2009 |
| JP | 51125675 | 11/1976 |
| JP | 07-060159 | 3/1995 |
| JP | 10 048215 A | 2/1998 |
| JP | 2955405 B2 | 10/1999 |
| JP | 2003-526786 | 9/2003 |
| JP | 2008-089499 A | 4/2008 |
| WO | WO 98/20019 | 5/1998 |
| WO | WO 01/67105 A1 | 9/2001 |
| WO | WO 2008/064854 A1 | 7/2008 |
| WO | 2008-298785 A | 12/2008 |
| WO | WO 2009/123148 A1 | 10/2009 |

OTHER PUBLICATIONS

European Search Report for EP Application No. 10831551.6 dated Apr. 5, 2013.
English-language International Search Report issued by the Japanese Patent Office in International Application No. PCT/JP2010/070369, mailed Dec. 21, 2010 (2 pages).

* cited by examiner

*Primary Examiner* — Erik B Crawford
*Assistant Examiner* — Gary E Hollinden
(74) *Attorney, Agent, or Firm* — Finnegan, Henderson, Farabow, Garrett & Dunner, L.L.P.

(57) ABSTRACT

Provided are an immunochromatography kit that is highly sensitive and capable of multicoloration, and organic colored microparticles that are ideal as an element of the immunochromatography kit. Organic colored microparticles having an average grain size between 10 and 1,000 nm and a color intensity between 1.0 and 5.0 are prepared using cellulose as the starting material. When the organic colored microparticles are used as a label in an immunochromatography kit, the immunochromatography kit is of a high sensitivity than conventional technology. The immunochromatography kit is also capable of multicoloration and is useful for rapid diagnosis.

8 Claims, No Drawings

ORGANIC COLORED MICROPARTICLES, DIAGNOSTIC REAGENT KIT CONTAINING THE SAME, AND IN VITRO DIAGNOSIS METHOD

This is a continuation of application Ser. No. 13/510,253, §371(c) date of May 16, 2012, which is the National Stage of PCT/JP2010/070369, filed Nov. 16, 2010, and claims the benefit of JP 2009-262004, filed Nov. 17, 2009 and JP 2010-161866, filed Jul. 16, 2010, all of which are incorporated herein by reference.

TECHNICAL FIELD

The present invention relates to organic colored microparticles derived from an organic polymer, a reagent kit using the microparticles, and an in vitro diagnosis method.

BACKGROUND ART

Microparticles composed of a polymer are used in various fields due to the ease of controlling their particle size, mechanical strength, particle size distribution, shape and degree of aggregation, examples of which include toner, anti-blocking materials of packing materials, insulating fillers, crystal nucleating agents, chromatographic fillers and abrasives. More recently, microparticles have also been applied to applications such as carriers for immunodiagnostic reagents, spacers of liquid crystal displays, standard particles for calibration of analytical equipment and standard particles for testing of porous films.

The amount of microparticles composed of a polymer used in immunodiagnostic reagent carrier applications in particular is increasing, and the amount used is increasing especially in diagnosis methods using immunochromatographic methods (to be referred to as "immunochromatography"). Although one of the foremost factors behind this increase is the release of large numbers of kits such as home pregnancy kits that are sold as quasi drugs and used by ordinary persons other than health care professionals, these increases have also been driven by a growing demand as means for various types of point-of-care testing (POCT: testing performed in proximity to a patient by a physician or other health care professional that enables results to be obtained rapidly) such as testing for various viruses such as adenovirus, rotavirus or norovirus, hepatitis B, hepatitis C and other types of hepatitis testing, or pathogen testing for pathogens such as *E. coli* O-157. The number of immunochromatographic tests performed is predicted to increase rapidly in the future in consideration of the growing number of influenza outbreaks in recent years. Microparticles are also being used for immunochromatography in various fields such as biochemical analyses, genetic analyses and other arbitrary analytical reactions in addition to immunodiagnostics.

Immunochromatography is carried out by, for example, selectively reacting an antibody or antigen (ligand) labeled with chromogenic microparticles composed of a metal colloid or colored latex derived from polystyrene with a test substance on a chromatography substrate, and developing while forming a complex. Next, an antigen or antibody (that which specifically binds with the aforementioned ligand) is immobilized in advance on a chromatography substrate at a prescribed detected location, and color is developed by capturing the developed complex. Although various methods have been examined and methods have been established for use as simple testing method, there is a desire to further increase sensitivity and accelerate the diagnostic process based on the need to reduce the burden on health care personnel in the clinical setting when performing POCT.

When diagnosing influenza, there are cases in which a positive result is not obtained by immunochromatography in the early stages of infection despite a positive result being obtained on the following day. It is necessary to further increase the sensitivity of testing in order to solve this problem. In addition, it is becoming increasingly common to simultaneously diagnose both type A antigen and type B antigen with a single immunochromatography kit. In such cases in which multiple specimens are present, although being able to simultaneously test a plurality of test substances with a single test leads to rapid diagnosis, it is also necessary to improve visibility to prevent erroneous diagnoses. Thus, it is preferable that different colors be generated (multicoloration) for each test substance when test substances are detected. Simultaneous diagnosis of multiple test substances using a single kit is also desirable when diagnosis various types of viral infections and when testing food safety, and similar multicoloration is considered to be effective in these applications as well.

The color generated in immunochromatography is derived from the substance used for labeling. In the case of metal colloids, since color is generated due to plasmon effects corresponding to the type of metal thereof, the resulting color is limited to a single color. For example, only red color is generated in the case of using gold colloid as described in Patent Document 1 indicated below. When assuming simultaneous testing of multiple parameters, although effects can be expected to a certain degree by making contrivances to the detected location, this cannot be said to be preferable from the viewpoints of visibility and preventing erroneous diagnoses.

In addition, in the case of metal colloids, a principle referred to as physical adsorption is typically used for the ligand binding method. Typical examples of ligand binding methods include physical adsorption, chemical bonding (covalent bonding), ionic bonding and inclusion. Physical adsorption refers to a binding method that utilizes hydrophobic interaction acting between a base material (such as chromogenic fine particles) and a material to be bound (such as a ligand). In actuality, various mechanisms such as electrostatic action, intermolecular forces and other mechanisms are thought to be acting in addition to hydrophobic interaction. Physical adsorption is advantageous in terms of ease of the procedure and cost since the procedure can be carried out more easily than other binding methods. However, in the case of physical adsorption, there are cases in which problems such as the absence of a fixed binding site and inhibition of adsorption in the presence of a surfactant can occur. In addition, there are also cases in which an adequate amount of ligand cannot be bound.

On the other hand, as disclosed in Patent Document 2 indicated below, in the case of using polystyrene or other latex particles, multicoloration is possible by using a chromophore composed of a disperse dye, oil-soluble dye or pigment. In addition, an arbitrary method such as physical adsorption or chemical bonding can be typically selected for the method used to bind the ligand. Consequently, problems associated with the aforementioned physical adsorption and the like can also be avoided. However, according to the examples disclosed in Patent Document 2, the dyeing capacity of the particles is low at about 6% by weight, and the resulting color intensity is weak. Consequently, in the case of using for immunochromatography, it is not possible to obtain distinct coloring effects, thereby resulting in a lack of reliability.

Although Patent Document 3 indicated below discloses microparticles obtained by staining cellulose, since the dyeing capacity relative to the amount of cellulose microparticles is low at about 20% by weight, the resulting stained microparticles are lightly colored. Although these microparticles are used in immunochromatography by imparting an antibody by physical adsorption or chemical bonding as described in Patent Document 4 indicated below, since the amount of antibody bound is insufficient and coloring of the microparticles per se is weak, distinct coloring results are unable to be obtained.

PRIOR ART DOCUMENTS

Patent Documents

Patent Document 1: Japanese Examined Patent Publication No. H7-60159
Patent Document 2: Japanese Patent No. 2955405
Patent Document 3: International Publication No. WO 2008/084854
Patent Document 4: International Publication No. WO 2009/123148

SUMMARY OF THE INVENTION

Problems to be Solved by the Invention

With the foregoing in view, an object of the present invention is to provide organic colored microparticles that are highly chromogenic and enable multicoloration, and to achieve high sensitivity of an immunochromatography kit by binding a ligand thereto and applying to a diagnostic reagent, and particularly an immunochromatographic reagent.

Means for Solving the Problems

As a result of conducting extensive studies and carrying out repeated experiments, the inventors of the present invention succeeded in obtaining microparticles having a deep color by using cellulose as a starting material. The inventors of the present invention surprisingly found that, as a result of staining cellulose to a deep color, ligand binding becomes possible by physical adsorption, and ligands can also be bound by covalent bonding by introducing reactive groups as necessary. It was also found that, when this was applied to immunochromatography by using as a carrier for a diagnostic reagent, increased sensitivity of the immunochromatography kit was able to be realized, thereby leading to completion of the present invention.

Namely, the present invention is as described below.

[1] Organic colored microparticles having an average particle size of 10 nm to 1000 nm and a color intensity of 1.0 to 5.0.

[2] The organic colored microparticles described in [1] above, wherein 10% by weight to 80% by weight of the organic colored microparticles constitute a coloring component.

[3] The organic colored microparticles described in [2] above, wherein the colored component is a dye.

[4] The organic colored microparticles described in any of [1] to [3] above, wherein 20% by weight to 90% by weight of the organic colored microparticles is derived from cellulose.

[5] The organic colored microparticles described in any of [1] to [4] above, wherein a ligand is bound by physical adsorption.

[6] The organic colored microparticles described in any of [1] to [5] above, having a reactive group.

[7] The organic colored microparticles described in [6] above, wherein the reactive group has a spacer structure having 3 or more atoms.

[8] The organic colored microparticles described in [6] or [7] above, wherein a ligand is bound to the reactive group by covalent bonding.

[9] A diagnostic reagent kit containing the organic colored microparticles described in any of [1] to [8] above.

[10] The diagnostic reagent kit according to claim [9], which is an immunochromatography kit.

[11] An in vitro diagnosis method comprising a step for using the organic colored microparticles described in any of [1] to [8] above.

[12] The in vitro diagnosis method described in [11] above, which is an immunochromatography method.

Effects of the Invention

The organic colored microparticles according to the present invention have extraordinarily superior coloring properties in comparison with the coloring properties of latex particles of the prior art, and since they are able to adsorb antigen and other ligands, they can be applied to immunochromatography. The organic colored microparticles according to the present invention are able to provide a highly sensitive immunochromatography kit as a result of actualizing coloring in the case of being captured with a selective and specific reaction, and as a result of enabling multicoloration, are useful for simultaneous measurement of multiple test substances. In addition, since the organic colored microparticles of the present invention enable the selection of an arbitrary method used to bind a ligand such as chemical bonding in addition to physical adsorption attributable to a dye, they can be applied to various test substances. Thus, the present invention enables rapid diagnoses with a low level of erroneous diagnosis, thereby greatly contributing to rapid diagnosis while also considerably expanding the application range of immunochromatography.

EMBODIMENTS OF THE INVENTION

<Average Particle Size>

The following provides a detailed explanation of the invention of the present application.

The microparticles in the present invention refer to organic colored microparticles having an average particle size of 10 nm to 1000 nm and a color intensity of 1.0 to 5.0. The preferable range of average particle size is 100 nm to 900 nm, and more preferably 200 nm to 800 nm. If the average particle size exceeds 1000 nm, development becomes slow when using in an immunochromatography kit, rapid evaluation is prevented, the microparticles are easily captured on the developing film, and the background per se becomes colored, thereby resulting in a tendency for the expected coloring at the detected location to be ambiguous. At a detected location in particular, there are many cases in which the pore size of the developing film becomes smaller due to coating of the capture reagent. Consequently, the label tends to be captured easily, or in other words, the rate of false positives increases. As a result, the test kit cannot be considered to be reliable.

<Color Intensity>

Color intensity in the present invention is defined as the value obtained by measuring visual absorbance of a dispersion of the organic colored microparticles at an optical path length of 10 mm using an integrating sphere in the range of 400 nm to 800 nm, subtracting the background component of the dispersion medium, obtaining an absorbance curve of the dispersion matrix per se, dividing the maximum value (ABS) thereof by the weight percentage of the dispersion matrix, and calculating per 0.01% by weight. Since the use of an integrating sphere makes it possible to reduce the effects of diffuse light on the particles, the resulting value can serve as an indicator of the degree of coloring of the microparticles, and a larger value thereof can be judged to indicate more distinct coloring. Although the color intensity of the microparticles of the present invention is 1.0 or more, the color intensity is preferably as high as possible. Color intensity can be increased either by using a dispersed dye or pigment that demonstrates a high degree of coloring, or selecting means for increasing the number times staining is carried out. However, since color intensity of 5.0 or more cannot be achieved with several rounds of staining using ordinary dyes, in consideration of economy, color intensity is preferably 1.0 to 5.0, more preferably 1.5 to 5.0 and even more preferably 2.0 to 5.0. In the case color intensity is lower than 1.0, visibility of a detected site becomes inferior when using in an immunochromatography kit due to weak coloring, thereby impairing reliability of test results.

<Material of Organic Colored Microparticles>

There are no particular limitations on the material of the organic colored microparticles in the present invention provided it has high color intensity and is stably dispersed. Although materials that can be deeply colored using dye or pigment can be applied, the realization of deep dyeing and strong dyeing is preferable when testing by immunochromatography and because this contributes to stabilization of kit quality during long-term storage. In order to achieve strong dyeing, for example, a covalently bonding reactive dye can be used, and a material derived from cellulose can be used that can be dyed with a reactive dye. Since microparticles composed of a material derived from cellulose have a large number of hydroxyl groups, not only are they able to retain numerous reactive dyes by covalent bonding, but they also are able to maintain a stable dispersion in water and the like after being deep dyed. For this reason, although the use of cellulose for the material of the organic colored microparticles is preferable, there are no particular limitations on the type thereof. For example, recycled cellulose, purified cellulose or natural cellulose can be used. Partially derivatized cellulose may also be used. Preferably 20% by weight to 90% by weight of the organic colored microparticles is derived from cellulose. More preferably, 20% by weight to 80% by weight of the organic colored microparticles is derived from cellulose. Even more preferably, 20% by weight to 70% by weight is derived from cellulose.

<Production Method of Material of Colored Organic Microparticles>

There are no particular limitations on the method used to produce the material of the organic colored microparticles in the present invention. Although the fine particles of a desired average grain size may be obtained by sizing, in the present invention, cellulose microparticles are prepared by using a congealing liquid obtained by dissolving cellulose in a good solvent thereof and mixing with water, organic solvent or ammonia and the like. The use of this method enables the grain size of the cellulose microparticles to be adjusted according to the composition of the congealing liquid. Although not intended to limit the production method of the material of the organic colored microparticles of the present invention, the following provides a detailed explanation thereof using a specific example.

First, linter cellulose is dissolved in a good solvent of cellulose. In the present invention, a cuprammonium solution prepared using a known method is used for the good solvent. A mixed system of organic solvent, water and ammonia is mainly used for the congealing liquid. Congealing is carried out by adding the prepared cuprammonium solution while stirring this congealing liquid. By then further regenerating by neutralizing with the addition of sulfuric acid, a slurry can be obtained that contains the target cellulose microparticles. A cellulose microparticle dispersion or cellulose microparticles can be obtained by diluting, purifying and drying this slurry.

<Coloring Method>

There are no particular limitations on the method used to color the material of the organic colored microparticles in the present invention, and various methods can be used, such as methods that use dyes or methods that use pigments. A method that uses a dye is particularly preferable in terms of increasing color intensity, and various types of dyeing agents can be used, such as a direct dye, metal-containing dye, acidic dye, basic dye, disperse dye, sulfide dye, vegetable dye or naphthol dye.

In the case of using cellulose microparticles for the organic colored microparticles in the present invention, since the surface area of the cellulose microparticles is considerably larger than the surface area of fibers, dyeing capacity can be made to be extremely large, and microparticles can be obtained in which 10% by weight or more of the organic colored microparticles is a coloring component. However, from the viewpoints of coloring properties and economy, the coloring component preferably accounts for 10% by weight to 80% by weight, more preferably 20% by weight to 80% by weight, and even more preferably 30% by weight to 80% by weight of the organic colored microparticles. Moreover, in the present invention, since cellulose microparticles can be dyed to a deep color and have superior long-term stability, or in other words, wet color-fastness, a reactive dye is preferably selected from the viewpoint of it being desirable to stain by covalent bonding.

The proportion of the coloring component relative to the organic colored microparticles in the present invention can be calculated from change in weight. In the present invention, although there may be cases in which all particles are unable to be recovered since staining is used for the coloring method and centrifugal separation is used during the course thereof, in this case, the proportion of the coloring component can be calculated from the weight of the particles able to be recovered and the weight of the particles before staining. For example, in the case of having stained 1.0 g of cellulose and 2.0 g of colored organic microparticles were obtained, the proportion of the coloring component is 50% by weight. In addition, the proportion of the coloring component can also be calculated by separating the organic microparticles and the coloring component by using a procedure for separating the organic colored microparticles and the coloring component as necessary, such as severing the covalent bonds by treating with acid or base, causing the microparticles to swell, or using another optimum cleaning procedure.

<Ligand>

The ligand in the present invention refers to a substance having the property of selectively and specifically binding to a specific test substance. Although there are no particular limitations on the type thereof, examples of ligands include antibodies, antigens, enzymes, genes, hormones, cells, nucleic acids, peptides and proteins.

<Physical Adsorption of Ligand by Staining>

A ligand can be physically adsorbed in the present invention simply by staining cellulose to a deep color using a dye. In cases in which physical adsorption performance in adequate with staining alone, hydrophobic and hydrophilic balance may be adjusted by combining with derivatization of cellulose as necessary. Although the reason why a ligand can be physically adsorbed simply by staining cellulose to a deep color is not clear, in general, although the degrees of hydrophilicity and hydrophobicity can be determined by measuring contact angle in the case of a film and the like, it is difficult to measure contact angle in the case of nanoparticles. Therefore, when contact angle was measured by staining Cellophane (Registered Trade Mark) used as a model of flat cellulose to a deep color, in contrast to the contact angle of the unstained cellulose being about 20 degrees to 30 degrees, the contact angle of adequately stained Cellophane (Registered Trade Mark) was able to be confirmed to have reached 40 degrees to 100 degrees in proportion to the dyeing capacity of the dye. Typical dyes such as benzene, naphthalene, anthraquinone or azo dyes have a strongly hydrophobic structure. In the present invention, as a result of a large amount of dye, which would ordinarily not be possible under fiber staining conditions, having bound to the cellulose, it is predicted that a degree of hydrophobicity was able to be attained that enabled physical adsorption of antibody. When bound mouse IgG antibody was measured using the Lowry method commonly used in protein assays, binding of antibody was able to be confirmed in the case of adequate staining as in the manner of the organic colored microparticles of the present invention. On the other hand, if staining intensity is excessively low, there was little difference observed between stained particles and unstained particles, and the amount of antibody bound tended to be low.

<Chemical Bonding of Ligand by Reactive Groups>

Chemical bonding can be selected for the ligand bonding method in addition physical adsorption in the present invention. In general, although physical adsorption offers the advantages of a simpler procedure and lower costs, it has also been indicated as having problems like those indicated below. Examples of such problems include a loss of reaction selectivity due to the ligand binding site not being constant, and bound ligand being removed by the presence of surfactant. Therefore, in order to solve these problems, a chemical bonding method may be employed that forms a covalent bond with a ligand corresponding to the circumstances. In addition, a chemical bonding method may be able to further increase the number of ligands bound as compared with physical adsorption.

<Reactive Groups>

Reactive groups in the present invention are used to covalently bond ligands. Typical examples of reactive groups include carboxyl group, amino groups, aldehyde groups, thiol groups, epoxy groups and hydroxyl groups. Although there are no particular limitations on the type thereof, carboxyl groups and amino groups are preferable. In the case of carboxyl groups, a covalent bond is formed with an amino group of a ligand using a carbodiimide. The time at which the reactive group is introduced may be prior to staining or after staining. The site where the reactive group is introduced may be organic microparticles or a stained portion. In addition, a portion of the structure of the dye may be used as a reactive group.

Introduction of reactive groups in the present invention can be confirmed with an infrared spectral analyzer. For example, in the case of a carboxyl group, absorption at about $1730\ cm^{-1}$ can be confirmed in the case of a free acid. In addition, in the case of an amino group, absorption at about $1600\ cm^{-1}$ can be confirmed in the case of a primary amino group. However, it is extremely difficult to quantify the amount of reactive groups introduced. This is due to the large amount of dye component present, thereby preventing quantification by ordinary quantification methods. In the present invention, an infrared spectral analyzer can only be used to determine whether or not a reactive group has been introduced.

<Spacer Structure>

Reactive groups in the present invention preferably have a spacer structure of three atoms or more. The inventors of the present invention found that, when a reactive group is introduced into highly colored organic colored microparticles, a ligand is covalently bound and then used in immunochromatography, sensitivity is further improved if the reactive group has a spacer structure of three atoms or more. Although the reason for this is unclear, the possibility has been considered that a selective reaction between the ligand and test substance is impaired by the effects of steric hindrance and charge of the dye that is present in a large amount.

A spacer structure refers to atoms present between the reactive groups and the organic colored microparticles. In addition, in the case the spacer structure is branched, it refers to the number of atoms of the main chain. For example, in the case of commonly known carboxymethyl cellulose, a portion of the hydroxyl groups of cellulose are substituted with carboxymethyl groups. The reactive groups in this case are the carboxymethyl groups, and the spacer structure becomes $-CH_2-$, namely a one atom spacer. In examples of the present invention, reactive groups having a spacer structure are introduced using the following four types of methods. The structures of compounds 1 to 4 are respectively indicated with Chemical Formulas 1 to 4. Although dye is also inherently bound to a portion of the hydroxyl groups, the dye is omitted from the formulas.

<Compound 1>

[Chemical Formula 1]

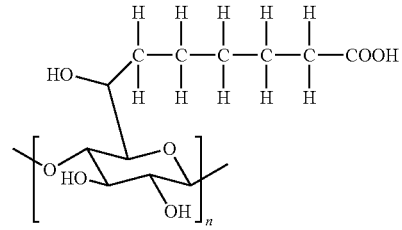

Stained cellulose microparticles and 5-hexenoic acid are allowed to react to introduce carboxyl groups. The number of atoms of the main chain, namely the number of atoms of the spacer structure, is 5.

<Compound 2>

[Chemical Formula 2]

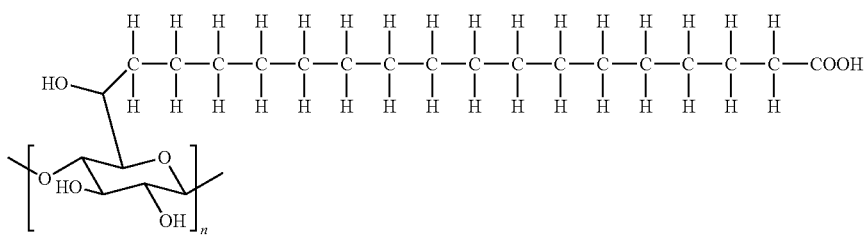

Stained cellulose microparticles and 16-heptadecenoic acid are allowed to react to introduce carboxyl groups. The number of atoms of the main chain, namely the number of atoms of the spacer structure, is 16.

<Compound 3>

[Chemical Formula 3]

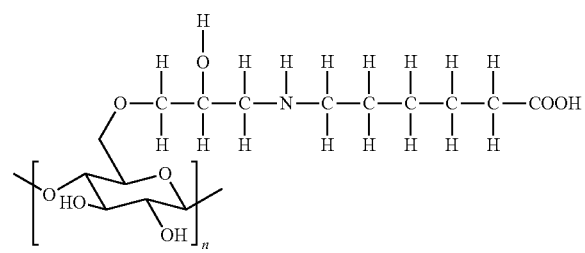

Stained cellulose microparticles and epichlorhydrin are allowed to react to introduce epoxy groups, and these are then further reacted with 6-aminohexanoic acid to introduce carboxyl groups. The number of atoms of the main chain, namely the number of atoms of the spacer structure, is 9.

<Compound 4>

[Chemical Formula 4]

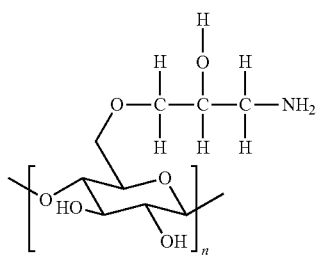

Stained cellulose microparticles and epichlorhydrin are allowed to react with introduced epoxy groups, and these are further reacted with ammonia to introduce primary amino groups. The number of atoms of the main chain, namely the number of atoms of the spacer structure, is 3.

Although the aforementioned spacer structures have a maximum number of atoms of 16, the spacer structure may be longer. Longer spacer structures can be achieved by changing the compound reacted with the stained cellulose microparticles, or the spacer structure can be additionally lengthened using an introduced reactive group. Although extremely long spacer structure can be introduced in theory, when considering from the viewpoints of ease of introduction and cost, the number of atoms is preferably 3 to 100, more preferably 3 to 50 and even more preferably 3 to 20.

<Dispersion Method of Organic Colored Microparticles>

Although organic colored microparticles obtained using the aforementioned coloring method, namely stained cellulose microparticles, can be used without ever drying by allowing to remain in the form of a dispersion, the dispersion may be stabilized by adding various types of reagents, surfactants and buffers. In addition, microparticles can be used alone or the dispersion can be adjusted to various concentrations by drying the dispersion as necessary. In the present invention, there are no particular limitations on the type of liquid in which the stained microparticles are dispersed provided it does not dissolve the microparticles or cause the microparticles to swell. Water, aqueous solutions of various inorganic compounds, alcohols, ethers, aldehydes, ketones, fatty acids, amines or other organic solvents can be used. A solvent may be used that is obtained by mixing various compounds at an arbitrary ratio, or these solvents can be used by mixing with a compatible hydrophobic solvent.

<Particle Size Distribution>

The grain size distribution of the organic colored microparticles of the present invention is determined with the following formula (1):

$$CV \text{ value} = (\text{standard deviation in volume grain size distribution as determined with a particle size analyzer})/(\text{volume average median diameter as determined with a particle size analyzer}) \times 100 \quad (1)$$

Although there are no particular limitations thereon, as was previously stated, since background coloring and false positives tend to be observed in an immunochromatography kit if grain size is excessively large, grain size distribution is preferably as small as possible, and is preferably 70% or less. Although the CV value can be adjusted according to the production conditions of the microparticles when desiring to make smaller, the particles may be sized by a procedure such as filtration or centrifugal separation at any stage before or after staining. In the present invention, in consideration of economy, the range of CV values is preferably 10% to 70%, more preferably 10% to 60% and even more preferably 10% to 50%.

<Immunochromatography>

The organic colored microparticles of the present invention are preferably used in an immunoassay based on immunochromatography.

Although the following provides an explanation of a typical example of immunochromatography, the present invention is not limited thereto, but rather can be applied to all sandwich assays in general. Generally speaking, immunochromatography involves preliminarily binding a label in the form of chromogenic microparticles composed of a metal colloid or colored latex derived from polystyrene to an antibody or antigen that specifically binds with an antigen or antibody serving as a test substance. On the other hand, an antibody or antigen that specifically reacts with an antigen or antibody is coated in lines at prescribed locations on a chromatography substrate. During testing, a complex is formed by contacting the labeled antibody or antigen with the antigen or antibody serving as the test substance, and although this complex is then developed on the chromatography substrate, this complex can be captured by primary antibody coated in the form of lines (sandwich assay). Since the label is also captured at this time, coloring occurs at the prescribed location. Since the presence of the test substance can be determined visually, this method has become widely popular in recent years as a simple test method. In addition, various types of testing can be performed by using not only an immune reaction using antigen or antibody, but also by using a ligand that specifically reacts with a test substance. In addition to immunodiagnostic reagents, immunochromatography is used in various other fields, such as biochemical analyses, genetic analyses and other arbitrary analytical reactions.

EXAMPLES

Although the following provides a detailed explanation of the present invention through examples thereof, the present invention is not limited to these examples.

First, a detailed explanation is provided of a method for measuring organic colored microparticles or a colored microparticle dispersion in the present invention.

All procedures were carried out in an environment at 25° C. unless specifically indicated otherwise.

(1) Particle Size (Particle Diameter) Distribution:

A cellulose microparticle dispersion was measured using the UPA-EX150 Nanotrac Particle Size Analyzer manufactured by Nikkiso Co., Ltd. Unless specifically indicated otherwise, water was used for the liquid in which the cellulose microparticles were dispersed, the cellulose microparticles were measured at a concentration of about 0.1% by weight, and the cumulative number of measurements was 30. In addition, CV values were calculated by dividing the standard deviation in volume grain size distribution as obtained by 30 rounds of measurement by the volume average median diameter.

(2) Color Intensity:

The optical absorbance of cellulose microparticles as well as colored polystyrene latex and gold colloid serving as comparative examples was measured using a combination of the SV-722 Integrating Sphere and the JASCOV-650 manufactured by Jasco Corp. The microparticles were measured at concentrations of 0.01% by weight to 0.1% by weight. Next, values calculated by dividing the maximum value of the absorbance peak (ABS) over a visible light range of 400 nm to 800 nm by the weight percentage of the microparticles were determined in 0.01% by weight increments.

(3) Confirmation of Introduction of Reactive Groups:

A microparticle dispersion introduced with reactive groups was dried to obtain microparticles introduced with reactive groups. The infrared absorption spectrum was measured by the reflection method using the Spectrum 100 Infrared Spectral Analyzer manufactured by Perkin Elmer Co., Ltd., and a comparison was made of the spectra before and after introduction of reactive groups. In the case of carboxyl groups, absorption of free acid of about 1730 $cm^{-1}$ was confirmed, while in the case of amino groups, absorption of primary amino groups of about 1600 $cm^{-1}$ was confirmed.

In addition, the M-110-E/H Hydraulic Ultra-high-pressure Homogenizer manufactured by the Microfluidics Corp. was used to break up aggregations of microparticles in the cellulose microparticle dispersion and stained cellulose microparticle dispersion. The treatment pressure at that time was 50 MPa, and the microparticles were passed through the chamber serving as the high-pressure portion of the homogenizer 10 times.

Example 1

Preparation of Microparticles

Linter cellulose was dissolved in a cuprammonium solution followed by diluting with water and ammonia to prepare a cuprammonium solution cellulose solution having a cellulose concentration of 0.37% by weight. The copper concentration of that solution was 0.13% by weight, and the ammonia concentration was 1.00% by weight. Next, a congealing liquid was prepared having a tetrahydrofuran concentration of 90% by weight and water concentration of 10% by weight. 500 g of the preliminarily prepared cuprammonium cellulose solution having a cellulose concentration of 0.37% by weight were then added while slowly stirring 5000 g of the congealing liquid using a magnetic stirrer. After continuing to stir for about 5 seconds, 1000 g of 10% by weight sulfuric acid were added to carry out neutralization and regeneration and obtain 26500 g of a slurry containing the target cellulose microparticles. The resulting slurry was then centrifuged for 10 minutes at a speed of 10000 rpm. The precipitate was removed by decantation, and deionized water was injected and stirred followed by centrifuging again. This procedure was repeated several times until the pH reached 6.0 to 7.0, after which dispersion treatment was carried out with a high-pressure homogenizer to obtain 150 g of a cellulose microparticle dispersion. Furthermore, all of the procedures were carried out in an environment at 25° C.

<Staining of Microparticles>

Next, the cellulose microparticles prepared in the manner described above were stained. 30 g of sodium sulfate and 1 g of Levafix Navy CA Gr. (Registered Trade Mark) manufactured by Dystar GmbH Corp. (to also be referred to as blue dye A) as reactive dye were added to 100 g of the cellulose microparticle dispersion adjusted to a microparticle concentration of 1.0% by weight, followed by heating to 60° C. using a constant temperature bath while stirring. After the temperature reached 60° C., 4 g of sodium carbonate were added followed by staining for 2 hours. Continuing, the resulting crudely stained microparticles were washed with a 5% by weight aqueous solution of sodium hydroxide, recovered by centrifugal separation, washed with pure water and then recovered by centrifugal separation. This series of procedures was defined as one cycle. These procedures were carried out for up to 3 cycles to obtain stained microparticles. The proportion of the dye component was 49% of the weight of the organic colored microparticles.

The results of measuring average grain size and color intensity before and after staining are shown in the following Table 1.

Example 2

Although the unstained cellulose microparticles obtained in Example 1 were stained using the same procedure, the procedure was carried out for a total of 10 cycles to obtain stained microparticles. The results of measuring average particle size and color intensity before and after staining are shown in the following Table 1.

Example 3

Cellulose microparticles and stained cellulose microparticles were obtained using the same method as Example 1 with the exception of using Levafix Rubine CA Gr. (Registered Trade Mark) manufactured by Dystar GmbH Corp. (to also be referred to as red dye B) as a reactive stain to stain the unstained cellulose microparticles obtained in Example 1. The results of measuring average grain size and color intensity before and after staining are shown in the following Table 1.

Example 4

Cellulose microparticles and stained cellulose microparticles were obtained using the same method as Example 1 with the exception of using for congealing a congealing fluid having a tetrahydrofuran concentration of 95% by weight and a water concentration of 5% by weight. The results of measuring average particle size and color intensity before and after staining are shown in the following Table 1.

Example 5

Cellulose microparticles and stained cellulose microparticles were obtained using the same method as Example 1 with the exception of using Levafix Rubine CA Gr.® manufactured by Dystar GmbH Corp. (red dye B) as a reactive stain to stain the unstained cellulose microparticles obtained in Example 4. The results of measuring average particle size and color intensity before and after staining are shown in the following Table 1.

Example 6

Cellulose microparticles and stained cellulose microparticles were obtained using the same method as Example 1 with the exception of using for congealing a congealing fluid having an acetone concentration of 26.5% by weight, an ammonia concentration of 0.20% by weight and a water concentration of 73.3% by weight. The results of measuring average particle size and color intensity before and after staining are shown in the following Table 1.

Comparative Example 1

Cellulose microparticles and stained cellulose microparticles were obtained using the same method as Example 1 with the exception of using for congealing a congealing fluid having a tetrahydrofuran concentration of 97% by weight and a water concentration of 3% by weight. The results of measuring average particle size and color intensity before and after staining are shown in the following Table 1.

Example 7

The stained cellulose microparticles obtained in Comparative Example 1 were filtered using a filtration film derived from nitrocellulose having pore size of 0.8 µm manufactured by Nihon Millipore K.K. followed by sampling the filtrate. The results of measuring average particle size and color intensity are shown in the following Table 1.

Example 8

Although stained microparticles were obtained by staining the unstained cellulose microparticles obtained in Example 1 using the same procedure as Example 1, only one cycle of the staining procedure was carried out. The results of measuring average particle size and color intensity before and after staining are shown in the following Table 1.

Example 9

Although stained microparticles were obtained by staining the unstained cellulose microparticles obtained in Example 1 using the same procedure as Example 1 with the exception using 0.5 g of Levafix Rubine CA Gr. (Registered Trade Mark) manufactured by Dystar GmbH Corp. (red dye B) for the reactive dye, only one cycle of the staining procedure was carried out. The results of measuring average particle size and color intensity before and after staining are shown in the following Table 1.

Comparative Example 2

Stained microparticles were obtained using the unstained microparticles obtained in Example 1 by carrying out the same procedure as Example 8 with the exception of using 0.2 g of Levafix Navy CA Gr. (Registered Trade Mark) manufactured by Dystar GmbH Corp. (blue dye A) for the reactive dye. The results of measuring average particle size and color intensity before and after staining are shown in the following Table 1.

Comparative Example 3

Stained microparticles were obtained using the unstained microparticles obtained in Example 6 by carrying out the same procedure as Example 8 with the exception of using 0.2 g of Remazol Black B HI-GRAN 150 (Registered Trade Mark) manufactured by Dystar GmbH Corp. (blue dye C) for the reactive dye. The results of measuring average particle size and color intensity before and after staining are shown in the following Table 1.

Comparative Example 4

Color intensity was measured using DS02B (Primary Blue (Registered Trade Mark), average grain size: 0.47 µm) manufactured by Bangs Laboratories, Inc. as stained polystyrene latex particles. The results are shown in the following Table 1.

Comparative Example 5

The results of measuring the color intensity of gold colloid particles having an average particle size of 0.04 µm are shown in the following Table 1.

TABLE 1

| | Uncolored | | Colored Particles | | | | |
|---|---|---|---|---|---|---|---|
| | Avg. particle size (nm) | CV value (%) | Avg. particle size (nm) | CV value (%) | Dye | Dyeing capacity (%) | Color intensity |
| Ex. 1 | 248 | 22 | 372 | 30 | Blue A | 49 | 2.9 |
| Ex. 2 | " | " | 494 | 40 | Blue A | 72 | 4.1 |
| Ex. 3 | " | " | 391 | 31 | Red B | 53 | 2.8 |
| Ex. 4 | 484 | 25 | 579 | 43 | Blue A | 45 | 3.2 |
| Ex. 5 | " | " | 590 | 30 | Red B | 41 | 2.6 |
| Ex. 6 | 44 | 19 | 62 | 31 | Blue A | 39 | 3.2 |
| Comp. Ex. 1 | 912 | 32 | 1105 | 51 | Blue A | 41 | 3.1 |
| Ex. 7 | " | " | 887 | 36 | " | " | 2.8 |
| Ex. 8 | 248 | 22 | 269 | 28 | Blue A | 20 | 1.6 |
| Ex. 9 | " | " | 270 | 25 | Red B | 13 | 1.2 |
| Comp. Ex. 2 | " | " | 255 | 25 | Blue A | 9 | 0.8 |
| Comp. Ex. 3 | 44 | 19 | 49 | 23 | Blue C | 8 | 0.6 |
| Comp. Ex. 4 | — | — | 470 | 22 | | | 0.4 |
| Comp. Ex. 5 | 40 | 31 | — | — | | | 2.2 |

<Performance Evaluation 1>

A performance evaluation was carried out by preparing immunochromatography kits using the stained, colored or chromogenic particles of Examples 1 to 9 and Comparative Examples 1 to 5.

<Preparation of Antibody-Bound Stained Microparticles by Physical Adsorption>

The stained or colored microparticles obtained in Examples 1 to 9 and Comparative Examples 1 to 4 were diluted with a phosphate buffer solution (to be referred to as "PBS") to a solid concentration of 1% by weight, 1 ml of the resulting 1% by weight phosphate buffer suspension of stained microparticles and 1 ml of diluted antibody obtained by diluting mouse-derived antibody to human chorionic gonadotropin (to be referred to as "hCG") (anti-hCG antibody #504 manufactured by Medix Biochemica Ab) with PBS to a concentration of 100 µg/ml were removed into an Eppendorf centrifuge tube and shaken for 2 hours at room temperature, and monoclonal antibody was bound to the stained microparticles, followed by centrifugally washing 3 times using PBS containing bovine serum albumin (BSA) at a concentration of 1% by weight and re-dispersing to a final volume of 2 ml to obtain an antibody-bound stained microparticle dispersion.

<Preparation of Antibody-Bound Gold Colloid>

200 ml of an aqueous gold chloride solution having a concentration of 0.01% by weight were boiled followed by the addition of aqueous sodium citrate solution having a concentration of 1% by weight thereto and continuing to heat and boil until the color of the solution changed from light yellow to violet-red to prepare a dispersion of the gold colloid particles having an average particle size of 0.04 μm indicated in Comparative Example 5. Next, 50 mM potassium dihydrogen phosphate solution was added to the resulting gold colloid dispersion to adjust the pH to 8, followed by adding monoclonal antibody to hCG at a rate of 10 μg per 1 ml of gold colloid dispersion, adding 0.1 ml of BSA (bovine serum albumin) having a concentration of 30% by weight to 10 ml thereof, centrifuging, removing the supernatant, washing by centrifuging and precipitating three times using PBS containing BSA at a concentration of 0.1% by weight, and re-dispersing to obtain an antibody-bound gold colloid particle dispersion.

<Preparation of Chromatography Substrate (Membrane)>

A test run antibody was sprayed and imprinted over a width of about 1 mm at a location 7 mm from one end (hereinafter indicating the lower end of a strip, with the other end indicating the upper end of the strip) of a commercially available membrane filter (HA120 manufactured by Nihon Millipore K.K., 25 mm×300 mm) using a liquid spraying device perpendicular to the direction of development, or in other words, parallel to the long side of the membrane. More specifically, mouse-derived anti-h α subunit antibody (#6601 manufactured by Medix Biochemica Ab) was used for the test run antibody, and a liquid prepared to a concentration of 0.5 mg/ml with PBS was sprayed at 1.0 μL/cm. In addition, a control line antibody was sprayed and imprinted over a width of 1 mm at a location 12 mm from the lower end in the same manner. More specifically, rabbit-derived anti-mouse antibody (Z0259 manufactured by Dako Group, Inc.) was used for the control line antibody, and a liquid prepared to a concentration of 0.5 mg/ml with PBS was sprayed at 1.0 μL/cm. After spraying each antibody, the substrates were dried for 1 hour followed by blocking using borate buffer solution containing milk casein, washing using Tris-HCl buffer containing sucrose, and fixing overnight at room temperature to prepare a chromatography membrane.

<Preparation of Chromatography Evaluation Samples>

A filter paper absorption pad measuring 20 mm×300 mm was contacted with the chromatography membranes using the resulting stained microparticles described in each of the examples and comparative examples at that their respective long sides so that they overlapped over a distance of 5 mm from the upper ends thereof, followed by cutting every 5 mm of width with a guillotine cutter to prepare samples. 60 samples can be obtained based on simple calculation.

<Chromatography Evaluation>

An hCG-containing samples used in a development test were prepared in the manner described below.

hCG was diluted with PBS containing BSA at a concentration of 1% by weight to contain hCG at concentrations of 100, 10 and 0 mIU/ml, respectively. A portion 2 mm from the lower end of the 5 mm wide kit samples obtained as described above was immersed in the sample solutions followed by development of the sample solutions. Ten minutes later, the coloring at the reaction site (label printed portion) on the membrane filter was observed visually. Evaluation criteria consisted of an evaluation of (−) in the case color was not observed at the test line, (+) in the case color was observed, (++) in the case coloring was clearly visible, and (+++) in the case of observing deep coloring. The evaluation results are shown in the following Table 2.

TABLE 2

| | After Staining | | | Test Line Coloring at Each Concentration (10 min) (mIU/ml) | | | |
|---|---|---|---|---|---|---|---|
| | Avg. particle size (nm) | Dye | Color intensity | 1000 | 100 | 10 | 0 |
| Ex. 1 | 372 | Blue A | 2.9 | +++ | +++ | ++ | − |
| Ex. 2 | 494 | Blue A | 4.1 | +++ | +++ | +++ | − |
| Ex. 3 | 391 | Red B | 2.8 | +++ | ++ | ++ | − |
| Ex. 4 | 579 | Blue A | 3.2 | +++ | ++ | ++ | − |
| Ex. 5 | 590 | Red B | 2.6 | +++ | ++ | + | − |
| Ex. 6 | 62 | Blue A | 3.2 | ++ | ++ | + | − |
| Comp. Ex. 1 | 1105 | Blue A | 3.1 | ++ | ++ | ++ | + |
| Ex. 7 | 887 | Blue A | 2.8 | ++ | ++ | + | − |
| Ex. 8 | 269 | Blue A | 1.6 | +++ | ++ | + | − |
| Ex. 9 | 270 | Red B | 1.2 | ++ | ++ | + | − |
| Comp. Ex. 2 | 255 | Blue A | 0.8 | + | − | − | − |
| Comp. Ex. 3 | 49 | Blue C | 0.6 | − | − | − | − |
| Comp. Ex. 4 | 470 | Blue | 0.4 | ++ | + | − | − |
| Comp. Ex. 5 | 40 | Red | 2.2 | +++ | + + | + | − |

Coloring of the control line was observed in all of the examples and comparative examples. At an hCG concentration of 100 mIU/ml, coloring of the test line was observed in Examples 1 to 9 and Comparative Examples 4 and 5. In addition, at an hCG concentration of 10 mIU/ml or less as well, coloring of the test line was observed in Examples 1 to 9 and Comparative Examples 4 and 5.

In Comparative Example 1, a phenomenon was observed in which apparent sensitivity decreased due to background coloring particularly at high antigen concentrations. In addition, a tendency was observed in which coloring occurred even in the absence of hCG in the samples, namely a tendency towards the occurrence of false positives. In Example 7, when the particles of Comparative Example 1 were used after filtering, although background coloring remained, false positives were no longer observed, thereby indicating that excessively large particle size leads to the occurrence of false positives. An excessively large particle size is unsuitable for diagnostic reagent kits. Since false positives were not observed in Examples 1 to 9, Examples 1 to 9 can be said to have high sensitivity.

On the other hand, in Comparative Examples 2 to 4, coloring was unable to be detected at an hCG concentration of 10 mIU/ml due to low color intensity of the dye. Thus, use of the organic colored microparticles of the present invention can be understood to have high sensitivity in comparison with polystyrene latex.

In addition, in a comparison with the gold colloid of Comparative Example 5, equal or higher sensitivity can be understood to be demonstrated by the inorganic colored microparticles of the present invention. Namely, use of the inorganic colored microparticles of the present invention enables highly sensitive diagnoses with blue color or red color.

<Introduction of Reactive Groups>

Continuing, reactive groups such as carboxyl groups or amino groups were introduced into the stained microparticles obtained in Example 1.

Example 10

Pure water and isopropyl alcohol (Wako Pure Chemical Industries, Ltd., reagent grade) were added to a portion of the blue stained microparticle dispersion obtained in Example 1 to adjust the ratio of isopropyl alcohol to water in the dispersion medium to 85:15 and the microparticle concentration in the dispersion medium to 0.50% by weight. 20 g of the resulting stained cellulose microparticle dispersion were placed in a test tube together with a rotor followed by attaching the test tube to a glass reflux tube. The cellulose microparticle dispersion was heated for 30 minutes in a water bath to a temperature of 50° C. while cooling by refluxing with tap water at about 10° C. Furthermore, heating was carried out while gently stirring using a magnetic stirrer. Subsequently, 74 mg of 40% by weight sodium hydroxide solution were added while stirring followed by continuing to stir for 30 minutes and then adding 216 mg of sodium chloroacetate (Wako Pure Chemical Industries, Ltd.). Carboxyl groups were introduced by continuing to stir and reflux for 3 hours. Three hours later, heating in the water bath was discontinued, a recovery flask was cooled with ice water, and the slurry was cooled after the reaction to a temperature of 20° C. After cooling, 1.0 g of 10% by weight hydrochloric acid was added while continuing to stir, to adjust the pH of the slurry after the reaction to an acidic pH. Dilution by decantation and deionized water was repeated several times using the same centrifuge as that used to wash the microparticles, the pH was adjusted to 6.0 to 7.0, and dispersion treatment was carried out with a high-pressure homogenizer to obtain a carboxylated stained microparticle dispersion. The results of measuring average particle size and color intensity for a portion of the resulting dispersion are shown in the following Table 3.

Example 11

Pure water and acetone (Wako Pure Chemical Industries, Ltd., reagent grade) were added to a portion of the blue stained microparticle dispersion obtained in Example 1 to adjust the ratio of acetone to water in the dispersion medium to 1:1 and the microparticle concentration in the dispersion medium to 1.0% by weight. 10 g of the resulting stained cellulose microparticle dispersion were placed in a test tube together with a rotor followed by attaching the test tube to a glass reflux tube. The cellulose microparticle dispersion was heated for 30 minutes in a water bath to a temperature of 40° C. while cooling by refluxing with tap water at about 10° C. Furthermore, heating was carried out while gently stirring using a magnetic stirrer. Subsequently, 705 mg of 5-hexenoic acid (Wako Pure Chemical Industries, Ltd.), 677 mg of cerium diammonium nitrate (Wako Pure Chemical Industries, Ltd.) and 617 ml of 1 mol/L nitric acid (Wako Pure Chemical Industries, Ltd.) were added. Carboxyl groups were introduced by continuing to stir and reflux for 3 hours. Treatment following the reaction was carried out in the same manner as Example 10 to obtain a carboxylated stained microparticle dispersion. The results of measuring average particle size and color intensity for a portion of the resulting dispersion are shown in the following Table 3.

Example 12

A carboxylated stained microparticle dispersion was obtained using the same method as Example 11 with the exception of using 1654 g of 16-heptadecenoic acid (Wako Pure Chemical Industries, Ltd.) for the reaction agent added to carry out carboxylation. The results of measuring average particle size and color intensity for a portion of the resulting dispersion are shown in the following Table 3.

Example 13

Pure water was added to a portion of the blue stained microparticle dispersion obtained in Example 1 to adjust the microparticle concentration in the dispersion medium to 1.0% by weight. 10 g of the resulting stained cellulose microparticle dispersion were placed in a test tube together with a rotor followed by attaching the test tube to a glass reflux tube. The cellulose microparticle dispersion was heated for 30 minutes in a water bath to a temperature of 35° C. while cooling by refluxing with tap water at about 10° C. Furthermore, heating was carried out while gently stirring using a magnetic stirrer. Subsequently, 571 mg of epichlorhydrin were added, followed by continuing to stir and reflux for 30 minutes to introduce epoxy groups. Subsequently, the temperature of the water bath was raised to 50° C. followed by the addition of 810 g of 6-aminohexanoic acid (Wako Pure Chemical Industries, Ltd.) and continuing to stir and reflux for 1 hour to introduce carboxyl groups. Treatment following the reaction was carried out in the same manner as Example 10 to obtain a carboxylated stained microparticle dispersion. The results of measuring average particle size and color intensity for a portion of the resulting dispersion are shown in the following Table 3.

Example 14

An aminated stained microparticle dispersion was obtained in the same manner as Example 13 with the exception of using 840 g of aqueous ammonia (Wako Pure Chemical Industries, Ltd.) for the reaction agent added to carry out introduction of epoxy groups. The results of measuring average grain size and color intensity for a portion of the resulting dispersion are shown in the following Table 3.

<Confirmation of Reactive Groups with Infrared Spectral Analyzer>

The carboxylated and aminated stained microparticle dispersions obtained in Examples 10 to 14 were dried to prepare carboxylated and aminated stained microparticles, and the introduction of reactive groups was confirmed with an infrared spectral analyzer. Absorption increased at about 1730 cm$^{-1}$ for the carboxylated stained microparticles and at about 1600 cm$^{-1}$ for the aminated stained microparticles, thereby confirming successful introduction of reactive groups.

TABLE 3

| | Type of Reactive Groups | Number of Atoms of Spacer Structure | Average particle size (nm) | CV value (%) | Color intensity |
|---|---|---|---|---|---|
| Example 10 | Carboxyl groups | 1 | 370 | 32 | 2.8 |
| Example 11 | Carboxyl groups | 5 | 375 | 33 | 2.6 |
| Example 12 | Carboxyl groups | 16 | 383 | 38 | 2.5 |
| Example 13 | Carboxyl groups | 9 | 380 | 34 | 2.6 |
| Example 14 | Amino groups | 3 | 374 | 31 | 2.7 |

<Performance Evaluation 2>

A performance evaluation was carried out by preparing immunochromatography kits after chemically bonding antibody to the stained microparticles introduced with reactive groups of Examples 10 to 14.

<Preparation of Antibody-Bound Stained Microparticles by Chemical Bonding 1>

A 2-morpholinoethanesulfonate buffer (to be referred to as "MES") having a pH of 5.2 and a concentration of 50 mM was prepared using 2-morpholinoethanesulfonic acid (Wako Pure Chemical Industries, Ltd.), sodium hydroxide and pure water, and 1-ethyl-3-(3-dimethylaminopropyl) carbodiimide hydrochloride (Wako Pure Chemical Industries, Ltd., to be referred to as "carbodiimide") was dissolved in MES buffer and adjusted to a carbodiimide concentration of 20% by weight. After precipitating the carboxylated stained microparticles obtained in Examples 10 to 13 using a centrifuge, the microparticles were re-dispersed in the MES buffer, and the solid concentration was adjusted to a concentration of 1% by weight to obtain carboxylated stained microparticle MES buffer dispersions. 1 g of 20% by weight carbodiimide solution was added to 10 g of the carboxylated stained microparticle MES buffer dispersions and allowed to react for 1 hour in an environment at 25° C. using a constant-temperature shaking water bath, followed by centrifuging for 30 minutes at a speed of 10,000 rpm following completion of the reaction. The precipitate was removed by decantation followed by addition of phosphate buffer and stirring to obtain carbodiimide-activated stained microparticles dispersed in phosphate buffer. Dilution with decantation phosphate buffer solution was repeated three times using the same centrifuge as that used to wash the microparticles to remove unreacted carbodiimide. The resulting carbodiimide-activated stained microparticles were then used to prepare antibody-bound stained microparticles by chemical bonding using the same procedure as that used to prepare antibody-bound stained microparticles by physical absorption.

<Preparation of Antibody-Bound Stained Microparticles by Chemical Bonding 2>

After precipitating the aminated stained microparticle dispersion using a centrifuge, the microparticles were re-dispersed in the aforementioned phosphate buffer and the solid concentration was adjusted to a concentration of 1% by weight to obtain an aminated stained microparticle PBS buffer dispersion. 1 g of 25% by weight glutaraldehyde solution (Wako Pure Chemical Industries, Ltd.) was added to 10 g of the aminated stained microparticle PBS buffer dispersion and allowed to react for 2 hours in an environment at 37° C. using a constant-temperature shaking water bath, followed by centrifuging for 30 minutes at a speed of 10,000 rpm following completion of the reaction. The precipitate was removed by decantation followed by addition of phosphate buffer and stirring to disperse glutaraldehyde-activated stained microparticles in phosphate buffer. Dilution with decantation phosphate buffer solution was repeated three times using the same centrifuge as that used to wash the microparticles to remove unreacted glutaraldehyde. The resulting glutaraldehyde-activated stained microparticles were then used to prepare antibody-bound stained microparticles by chemical bonding using the same procedure as that used to prepare antibody-bound stained microparticles by physical absorption. Unreacted aldehydes were removed by adding 1 g of glycine prior to adding bovine serum albumin at a concentration of 0.1% by weight.

<Chromatography Evaluation>

The antibody-bound stained microparticles by chemical bonding obtained in Examples 10 to 14 and the antibody-bound stained microparticles by physical absorption obtained in Example 1 were evaluated for use as immunochromatography microparticles.

Evaluations were carried out using the same procedure as previously described, and three levels of hCG concentrations were used consisting of 10, 1 and 0 mIU/ml. The evaluation results are shown in the following Table 4.

TABLE 4

| | After Staining | | | Test Line Coloring at Each Concentration (10 min) (mIU/ml) | | |
|---|---|---|---|---|---|---|
| | Avg. particle size (nm) | Color intensity | Antibody Binding Method | 10 | 1 | 0 |
| Example 1 | 372 | 2.9 | Physical adsorption | ++ | − | − |
| Example 10 | 370 | 2.8 | Chemical bonding | ++ | − | − |
| Example 11 | 375 | 2.6 | Chemical bonding | ++ | + | − |
| Example 12 | 383 | 2.5 | Chemical bonding | ++ | ++ | − |
| Example 13 | 380 | 2.6 | Chemical bonding | ++ | + | − |
| Example 14 | 374 | 2.7 | Chemical bonding | ++ | + | − |

Coloring was observed for the antibody-bound stained microparticles in which antibody was bound by chemical bonding of Examples 11 to 14 even at an hCG concentration of 1 mIU/ml. In each of these cases, the number of atoms of the spacers of the reactive groups was 3 or more. In contrast, coloring was not observed for the stained microparticles in which antibody was bound by physical adsorption of Example 1 or for the antibody-bound stained microparticles of Example 9 in which the number of atoms of the spacer was 1 at an hCG concentration of 1 mIU/ml. On the basis of these results, the organic colored microparticles of the present invention were determined to be able to support a ligand by chemical bonding.

INDUSTRIAL APPLICABILITY

The organic colored microparticles of the present invention are useful for use as a label for immunodiagnosis and immunochromatography, and can be preferably used in a highly sensitive immunochromatography kit that allows rapid evaluation.

The invention claimed is:

1. Colored cellulose microparticles for use in an immunochromatography kit,
   wherein the colored cellulose microparticles have an average grain size of 10 nm to 1000 nm and a color intensity of 1.0 to 5.0,
   wherein 10% by weight to 80% by weight of the colored cellulose microparticles constitute a coloring component which is a reactive dye, and
   said color intensity being obtained by:
      preparing a dispersion consisting of the colored cellulose microparticles in water as a dispersion medium at a concentration ranging from 0.01% to 0.1% by weight,
      measuring the optical absorbance of said dispersion between 400 and 800 nm using a combination of the SV-722 Integrating Sphere and the JASCO-V-650 manufactured by Jasco Corp and an optical path of 10 mm, thereby obtaining a sample absorbance curve, measuring the optical absorbance of the dispersion medium between 400 and 800 nm using said integrating sphere and an optical path of 10 mm, thereby obtaining a background absorbance curve, subtracting the background absorbance curve from the sample absorbance curve, thereby obtaining a corrected absorbance curve, said corrected absorbance curve having a peak with a maximum absorbance value, and dividing the maximum absorbance value of the peak of the corrected absorbance curve by the concentration in % by weight of the dispersion, and then standardized per 0.01% by weight, thereby obtaining the color intensity.

2. The colored cellulose microparticles according to claim 1, wherein a ligand is bound by physical adsorption.

3. The colored cellulose microparticles according to claim 1, having a reactive group.

4. The colored cellulose microparticles according to claim 3, wherein the reactive group has a spacer structure having 3 or more atoms.

5. The colored cellulose microparticles according to claim 3, wherein a ligand is bound to the reactive group by covalent bonding.

6. An immunochromatography kit for detecting a first antigen or antibody as a test substance, the improvement comprising as a label, the colored cellulose microparticles according to any one of claims 1, and 2 to 5, wherein said microparticles are bound to a second antibody or antigen that specifically binds to said first antigen or antibody, and a chromatography substrate coated with a third antibody or antigen that specifically binds to said first antigen or antibody.

7. An immunochromatography kit for detecting a test substance, the improvement comprising as a label, the colored cellulose microparticles according to any one of claims 1, and 2 to 5, wherein said microparticles are bound to a first ligand that specifically binds to said test substance, and a chromatography substrate coated with a second ligand that specifically binds to said test substance.

8. The immunochromatography kit of claim 7, wherein the first ligand and the second ligand are antibodies, antigens, enzymes, genes, hormones, cells, nucleic acids, peptides, or proteins.

* * * * *